United States Patent
Aripin et al.

(10) Patent No.: US 10,688,146 B2
(45) Date of Patent: Jun. 23, 2020

(54) *CURCUMA MANGGA* VAL ET. ZIPP. EXTRACT AS A TREATMENT TO OVERCOME PROSTATE PROBLEMS

(71) Applicant: PT DEXA MEDICA, Tangerang Selatan (ID)

(72) Inventors: Asep Aripin, Karawang (ID); Agung Heru Karsono, Jakarta Timur (ID); Olivia Mayasari, Jakarta Utara (ID); Priska Hardadi, Bekasi (ID); James M. Sinambela, Bekasi (ID); Raymond R. Tjandrawinata, Jakarta Selatan (ID)

(73) Assignee: PT Dexa Medica, Tangerang (ID)

( * ) Notice: Subject to any disclaimer, the term of this patent is extended or adjusted under 35 U.S.C. 154(b) by 0 days.

(21) Appl. No.: 15/984,529

(22) Filed: May 21, 2018

(65) Prior Publication Data
US 2018/0264070 A1 Sep. 20, 2018

Related U.S. Application Data

(63) Continuation of application No. 14/894,615, filed as application No. PCT/ID2014/000004 on Jun. 3, 2014, now abandoned.

(30) Foreign Application Priority Data

Jun. 4, 2013 (ID) .............................. P00201300419

(51) Int. Cl.
| | |
|---|---|
| *A61K 36/9066* | (2006.01) |
| *A61K 9/00* | (2006.01) |
| *A23L 33/105* | (2016.01) |
| *A23L 2/52* | (2006.01) |
| *A61K 9/46* | (2006.01) |
| *A61K 9/02* | (2006.01) |
| *A61K 9/06* | (2006.01) |
| *A61K 9/08* | (2006.01) |
| *A61K 9/10* | (2006.01) |
| *A61K 9/107* | (2006.01) |

(52) U.S. Cl.
CPC ............ *A61K 36/9066* (2013.01); *A23L 2/52* (2013.01); *A23L 33/105* (2016.08); *A61K 9/0053* (2013.01); *A61K 9/0095* (2013.01); *A23V 2002/00* (2013.01); *A61K 9/006* (2013.01); *A61K 9/0007* (2013.01); *A61K 9/0014* (2013.01); *A61K 9/0019* (2013.01); *A61K 9/0031* (2013.01); *A61K 9/02* (2013.01); *A61K 9/06* (2013.01); *A61K 9/08* (2013.01); *A61K 9/10* (2013.01); *A61K 9/107* (2013.01); *A61K 2236/00* (2013.01)

(58) Field of Classification Search
None
See application file for complete search history.

(56) References Cited

U.S. PATENT DOCUMENTS

| | | | | |
|---|---|---|---|---|
| 6,224,877 B1 * | 5/2001 | Gaikar | ............... | A61K 36/9066 424/756 |
| 2010/0239553 A1 * | 9/2010 | Bartunek | ............. | A61K 31/195 424/94.1 |

OTHER PUBLICATIONS

Abas et al. (2005) J. Nat. Prod. 68: 1090-1093. (Year: 2005).*
Website document entitled "How Curcumin Can Fight Prostate Cancer and Inflammation" (available at https://prostate.net/articles/curcumin-turmeric-prostate-cancer-and-bph/). Downloaded from website May 7, 2019 (Year: 2019).*
Jitoe et al. (1992) J. Agric. Food Chem. 40: 1337-1340. (Year: 1992).*
Kim et al. (2015) BMC Complementary and Alternative Medicine 15: 380 (7 pages). (Year: 2015).*
Ledda et al. (2012) Panminerva Med. 54 (Suppl. 1 to No. 4): 17-22. (Year: 2012).*
Liu et al. (2012) Food Chemistry 135: 634-640. (Year: 2012).*
Malek et al. (2011) Molecules 16, 4539-4548. (Year: 2011).*
Raskin et al. (2004) Current Pharmaceutical Design 10, 3419-3429. (Year: 2004).*
Revilla et al. (1998) J. Agric. Food Chem. 46: 4592-4597. (Year: 1998).*
Shi et al. (2009) Anti-Cancer Agents in Medicinal Chemistry 9: 904-912. (Year: 2009).*
Karsono et al. (2014) Cancer Management and Research, 6: 267-278. (Year: 2014).*

* cited by examiner

*Primary Examiner* — Terry A McKelvey
*Assistant Examiner* — Norussell G Fiebig
(74) *Attorney, Agent, or Firm* — Neifeld IP Law

(57) ABSTRACT

A preparation comprises a herbal extract and/or fraction, and a pharmaceutical preparation includes extract of *Curcuma mangga* Val. et Zipp., which has bioactivities in reducing expression levels of 5-alpha-reductase-1, androgen receptor, and PI3 in prostate cancer cells. The use of this present invention is directed to reduce prostate enlargement. Moreover, it also can be used to treat prostate cancer, lung cancer, and other diseases related to GPCR pathway.

4 Claims, 9 Drawing Sheets

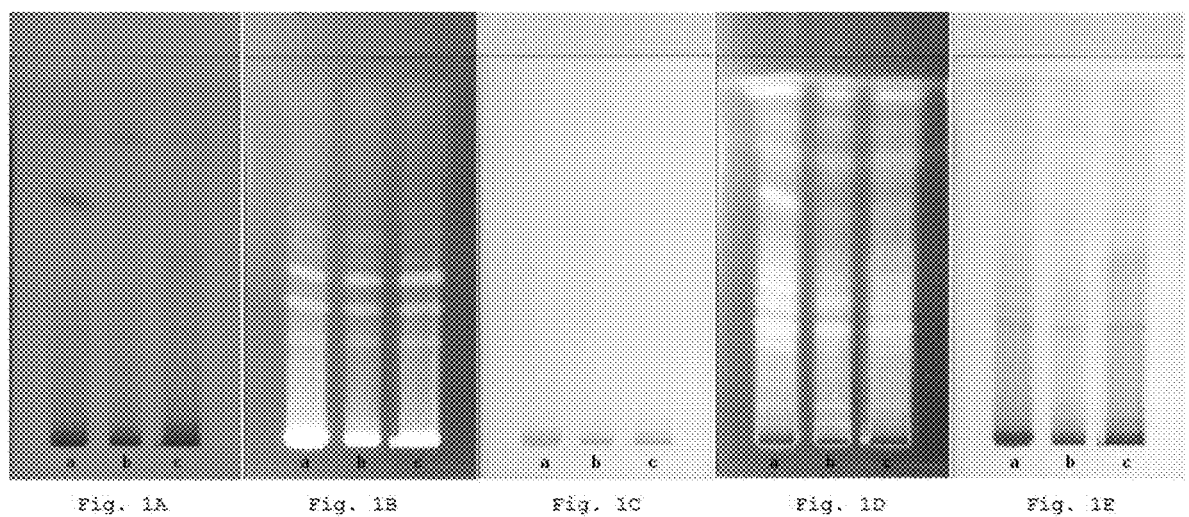
Thin Layer Chromatography (TLC) profile of *Curcuma mangga* Val. et Zipp. extract

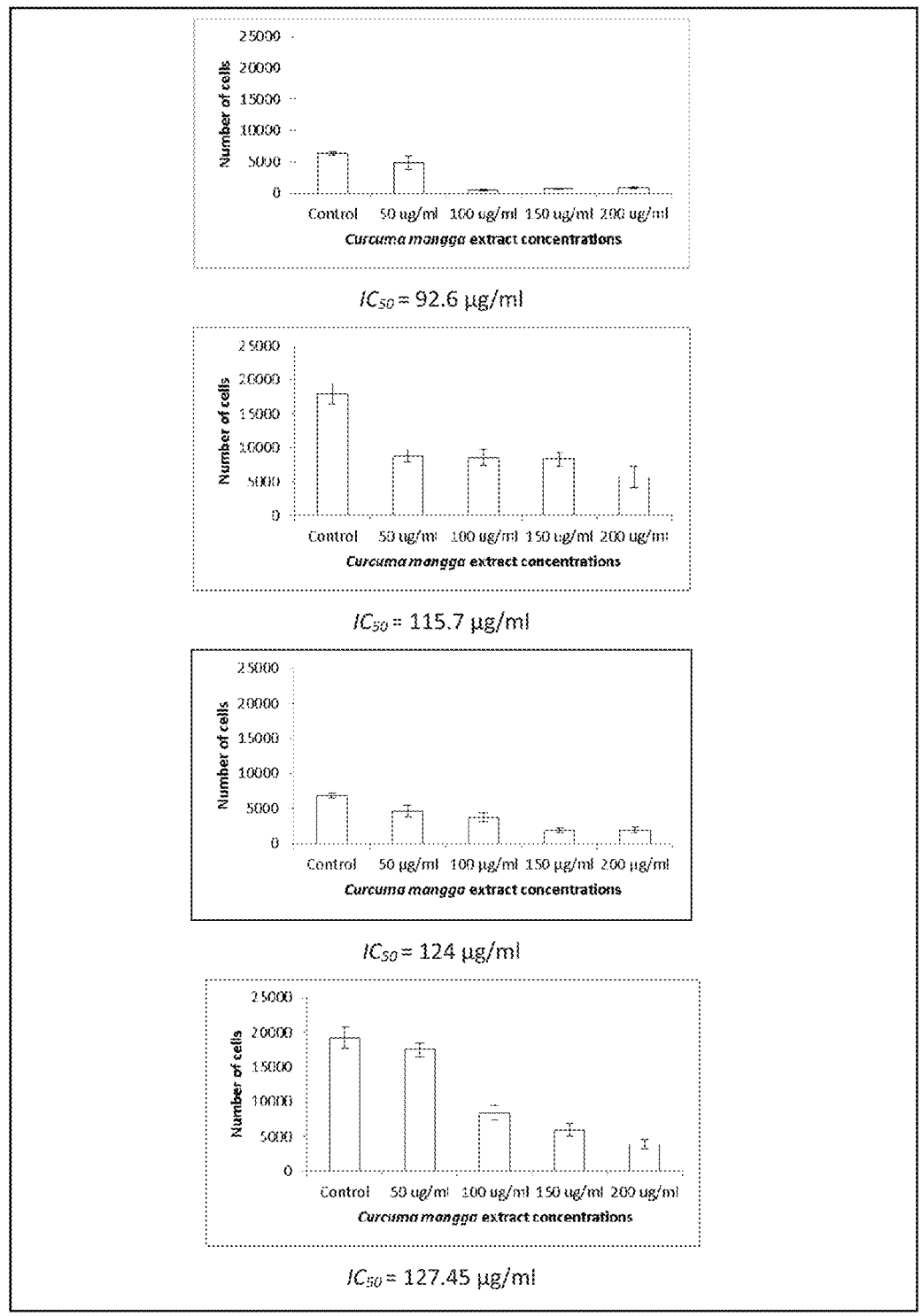
Figure 2. The effect of *Curcuma mangga* Val. et Zipp extract against PC3 cells proliferation

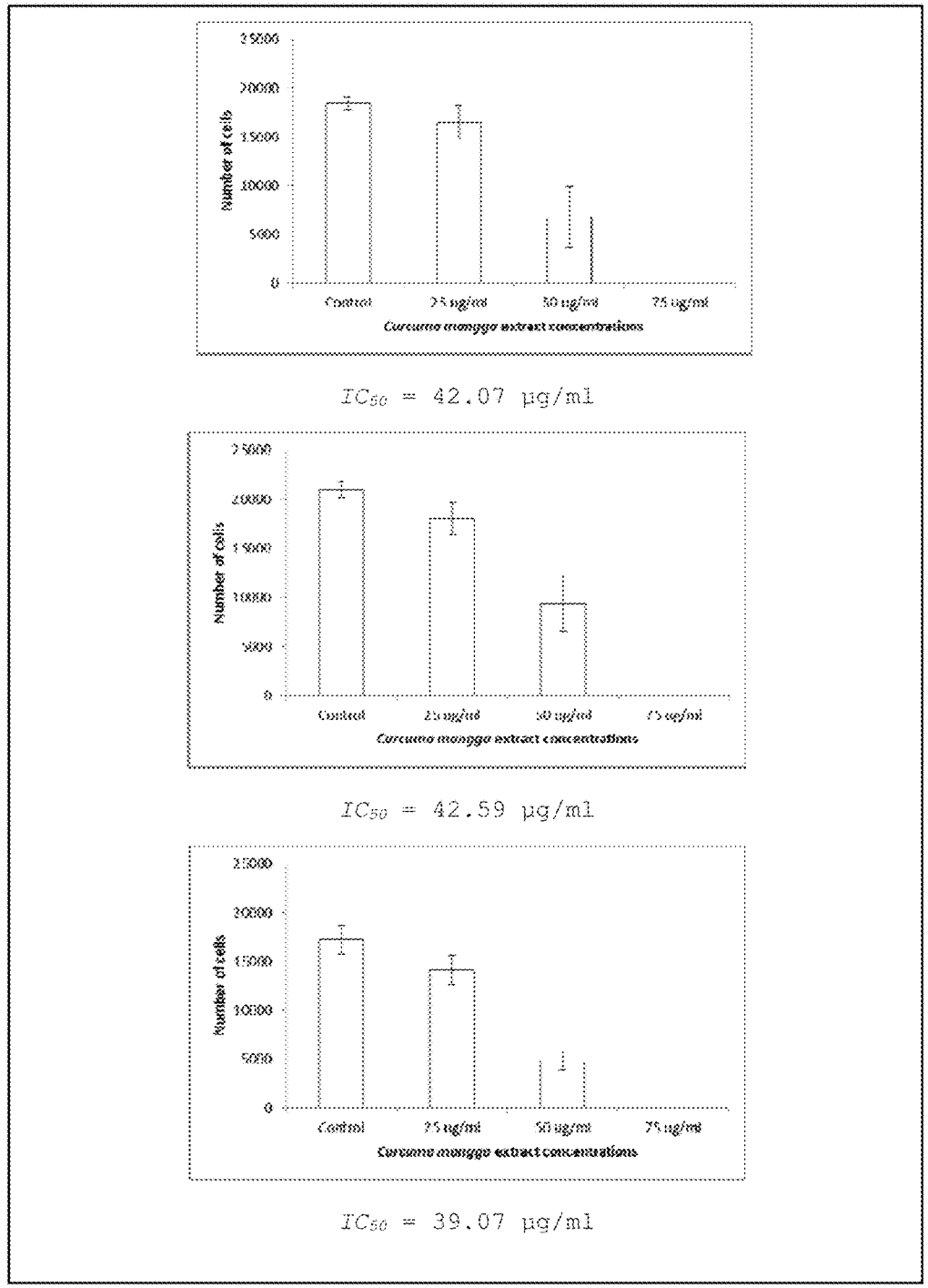
Figure 3. The effect of *Curcuma mangga* Val. et Zipp extract against A549 cells proliferation

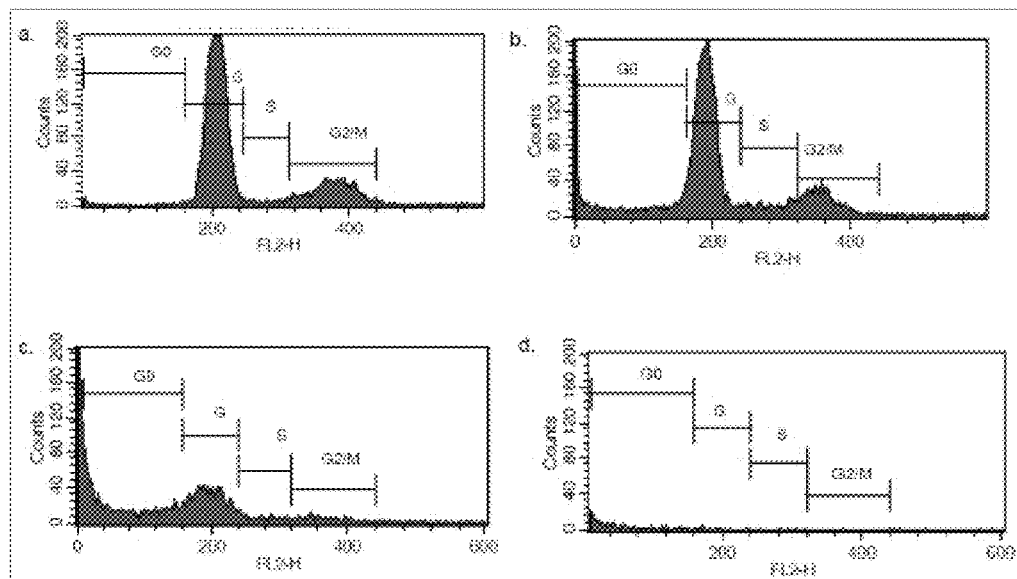
Figure 4. Result of FACS experiment a.) Control treatment b.) Treatment with extract of *Curcuma mangga* Val. et Zipp. 50 μg/ml c.) Treatment with extract of *Curcuma mangga* 100 μg/ml d.) Treatment with extract of *Curcuma mangga* Val. et Zipp. 150 μg/ml
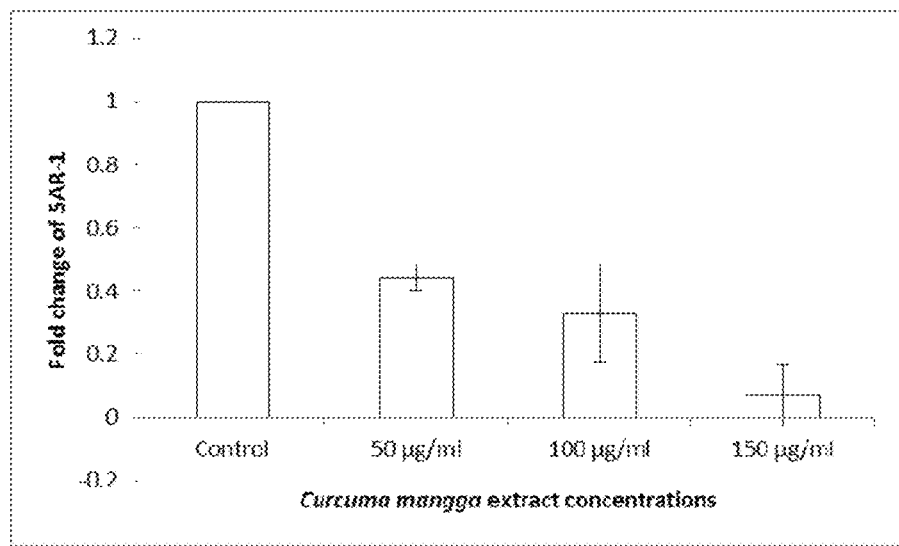
Figure 5. qPCR results of 5-alpha-reductase-1 genes in PC3 cells after the administration of *Curcuma mangga* Val. et Zipp. extract

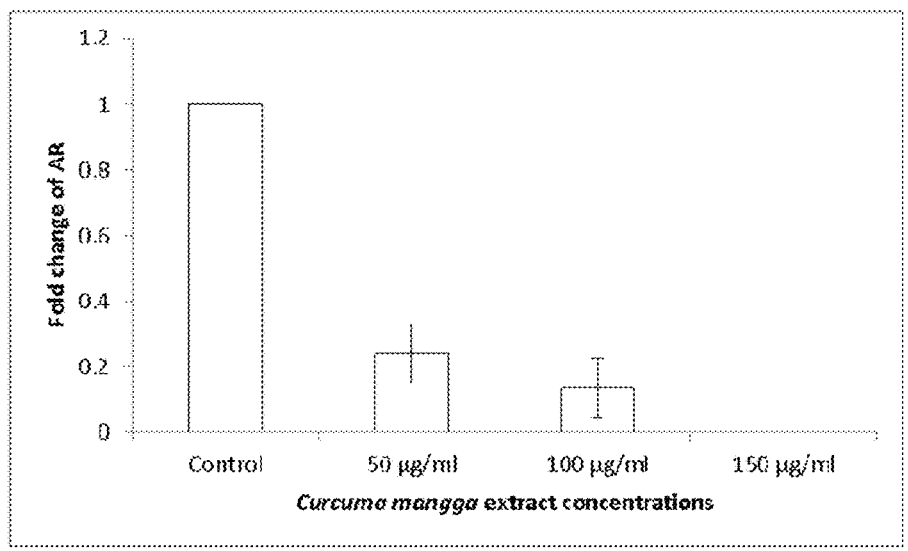
Figure 6. qPCR results of receptor androgen genes in PC3 cells after the administration of *Curcuma mangga* Val. et Zipp. extract
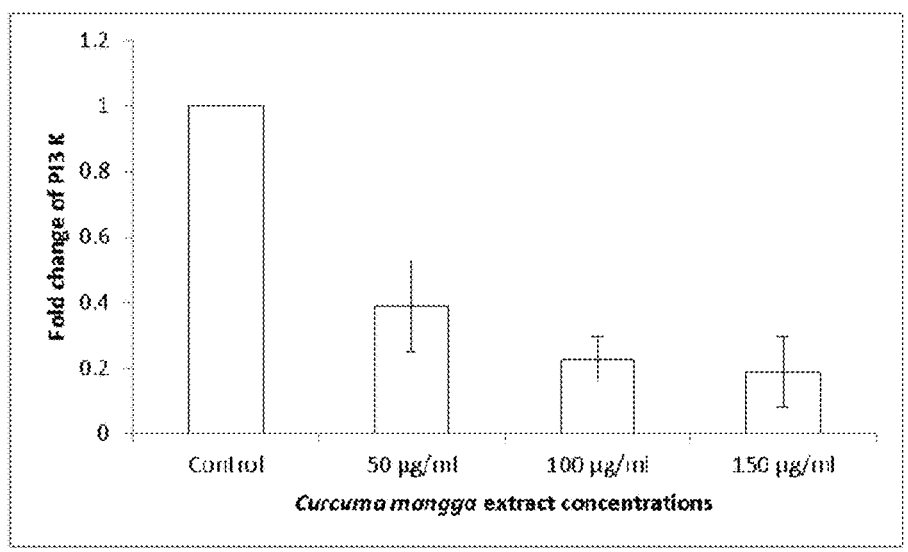
Figure 7. qPCR results of PI3 Kinase genes in PC3 cells after the administration of *Curcuma mangga* Val. et Zipp. extract

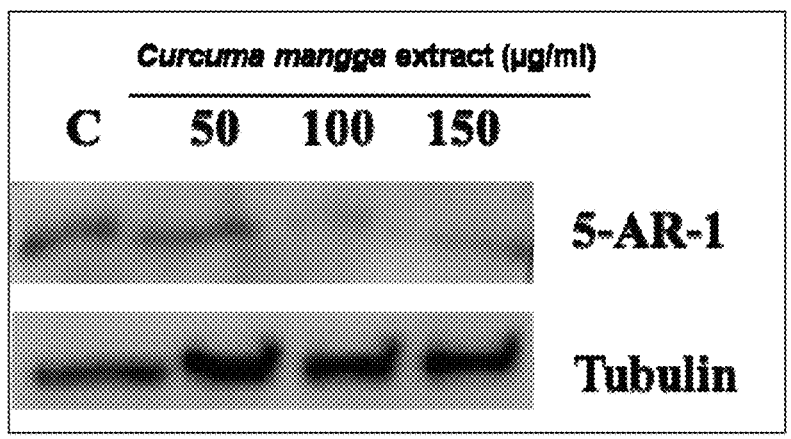
Figure 8. Western Blot results of 5-alpha-reductase-1 in PC3 cells after the administration of *Curcuma mangga* Val. et Zipp. extract
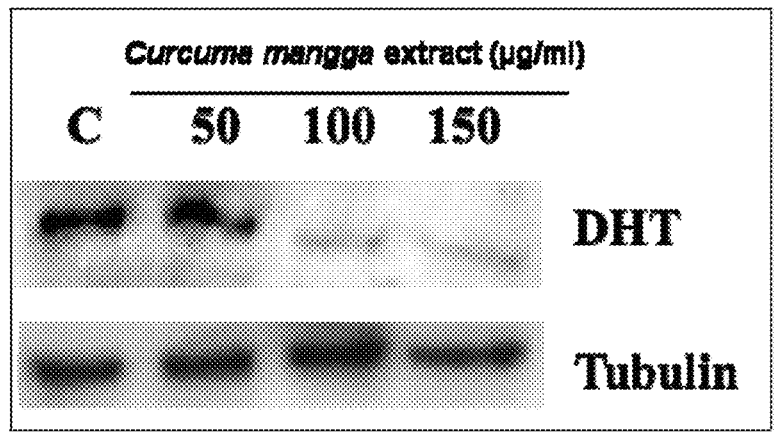
Figure 9. Western Blot results of Dihydrotestosterone (DHT) in PC3 cells after the administration of *Curcuma mangga* Val. et Zipp. extract

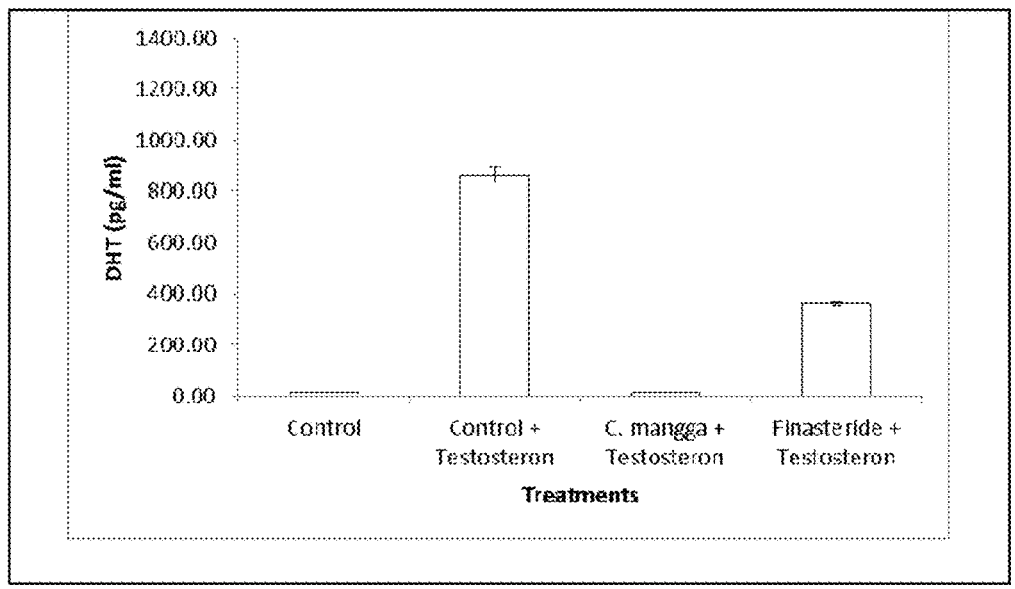
Figure 10. Effect of *Curcuma mangga* Val. et Zipp extract against the levels of DHT
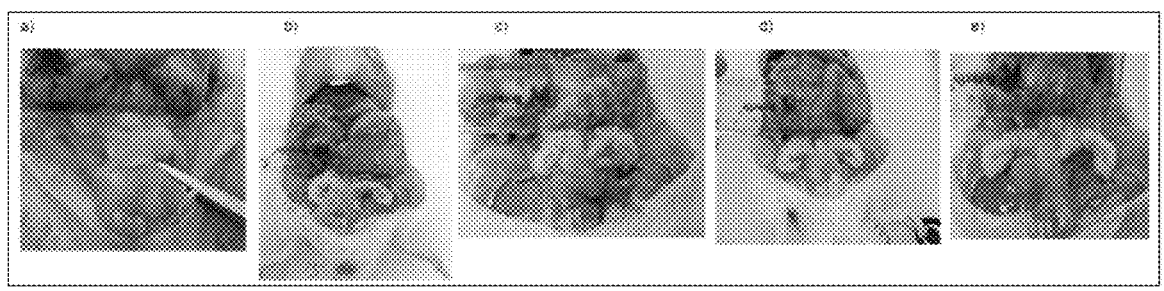
Figure 11. Results of *Curcuma mangga* Val. et Zipp. extract administration to rats that had experienced prostate gland enlargement

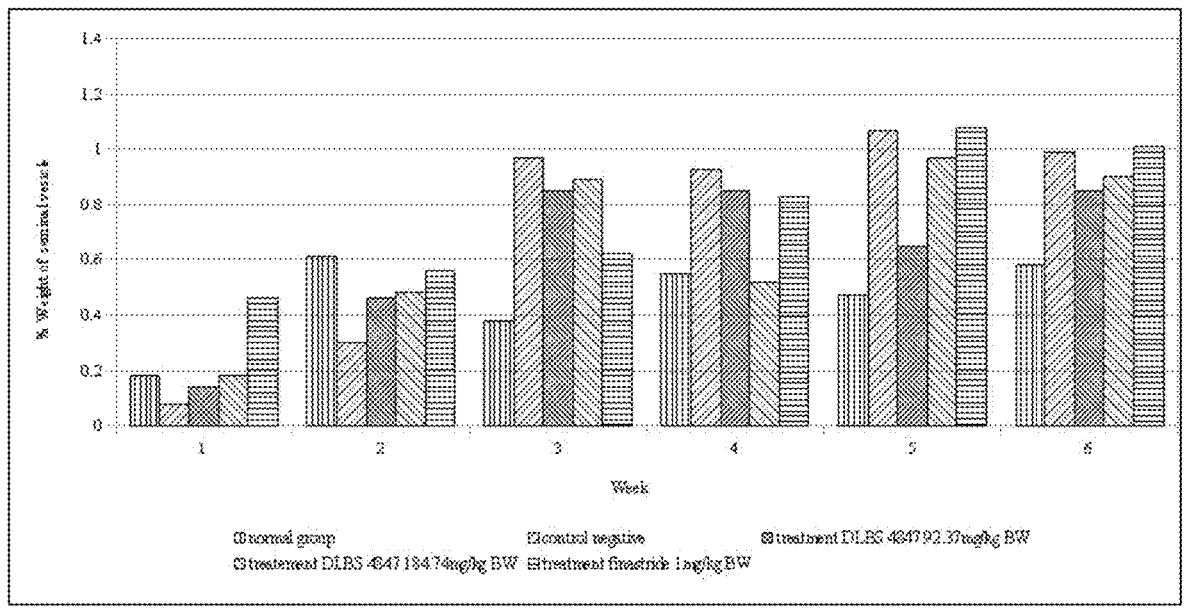
Figure 12. Graphic of the percentage of seminal vesicle weight development of rats as experimental animals
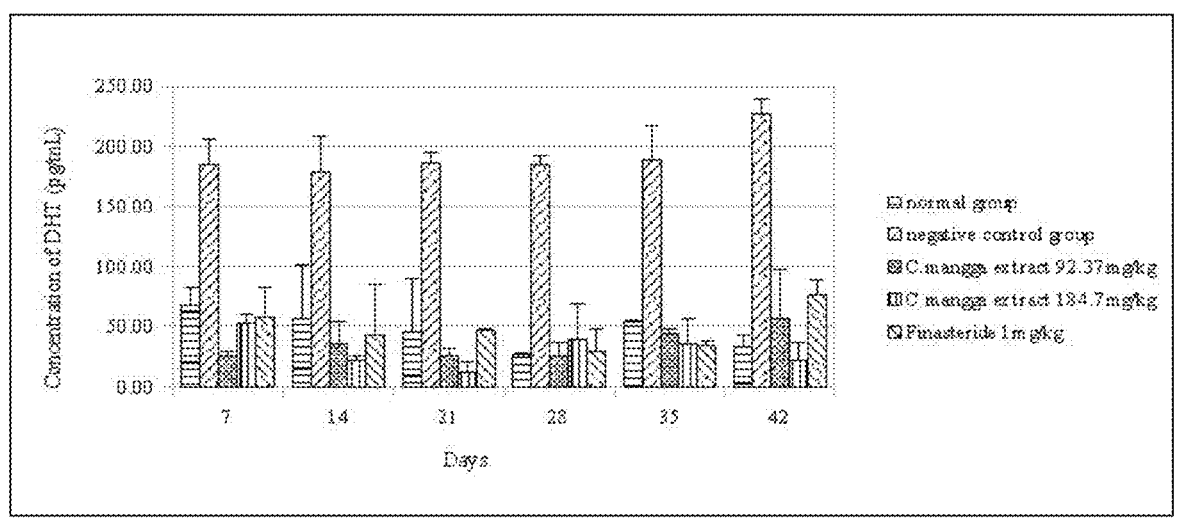
Figure 13. Graphic of DHT plasma concentrations (pg/mL) of each experimental animals group

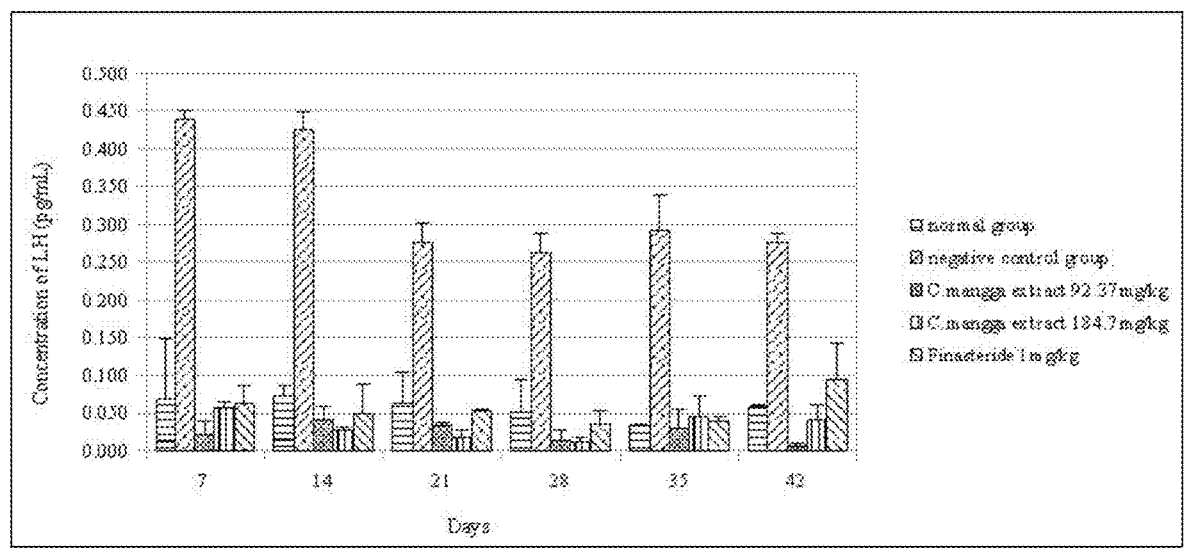
Figure 14. Graphic of LH plasma concentrations (pg/mL) of each experimental animals group

CURCUMA MANGGA VAL ET. ZIPP. EXTRACT AS A TREATMENT TO OVERCOME PROSTATE PROBLEMS

CROSS REFERENCE TO RELATED APPLICATIONS

This application is a division of U.S. application Ser. No. 14/894,615, filed Nov. 30, 2015, which is a 371 National Stage Entry of PCT/ID2014/000004 filed Jun. 3, 2014, and PCT/ID2014/000004 claims priority to Indonesian Application P00201300419, filed Jun. 4, 2013. The contents of U.S. application Ser. No. 14/894,615, filed Nov. 30, 2015, is incorporated by reference in its entirety.

FIELD OF THE INVENTION

The present invention relates to the herbal extract from *Curcuma mangga* Val et. Zipp. plant, including the extraction method and the description of biological activity of the extract, which show its ability to overcome the problem of prostate enlargement.

BACKGROUND OF THE INVENTION

Prostate is a small gland only found in men and forms a part of the reproduction system. The role of the gland is in the forming of semen, namely sperm carrier fluid. Prostate gland is generally grows with age. However, the development of prostate gland can become a problem when it becomes sufficiently large to suppress the urethra. Benign Prostatic Hyperplasia (BPH) is a term for prostate growth which causes problems (Guess 2001: 152).

In general, BPH occurs in men over 40 years old. The enlargement of prostate results in the obstruction of the urethra, thus the process of urine excretion becomes disrupted and slower, and frequently becomes difficult to urinate. If left untreated, it will result in the emergence of urinary tract infection and kidney damage. The enlargement will begin to occur at epithelial and stromal tissues in the prostate gland. The enlargement of prostate gland is caused by abnormal changes in the process of cell growth. If the disease is not treated properly, it will increase the risk of prostate cancer (Guess 2001: 152; Beckman et al. 2005: 1356; Fine & Ginsberg 2008: 333).

Currently, prostate cancer is the second leading cause of death from cancer in the United States (Talcot et al. 2011: 1046; Fei Ye et al. 2007: 100). According to Winter et. al. (2001: 1227), the possibility of developing prostate cancer among men is one in 55 men aging 40-59 years and one in six men aging 60-79 years. Therefore, early treatment is necessary to prevent prostate cancer from getting worse.

Until now, there are two types of available treatments to overcome BPH i.e. through medical therapy and surgery. Treatment through common medical therapy is using alpha-blocker and 5-alpha-reductase enzyme inhibitors. However, these two types of chemical drugs that currently available are known to have certain side effects, including orthostatic hypotension, dizziness, and weakness (Gjertson et al. 2004: 869). Therefore, the present invention, namely the extract of *Curcuma mangga* Val. et Zipp., which is derived from natural ingredients, is expected to be one alternative source and a new treatment that can replace those drugs.

Treatment of the enlargement of prostate gland that has grown into prostate cancer should be conducted by adjusting the treatment with the stage of the prostate cancer. Prostatectomy or radiotherapy can be done to treat low risk prostate cancer. For severe conditions, a combination of low risk medication and adjuvant androgen suppressive can be used as a treatment (Sanda & Kaplan 2009: 2141). The present invention is indicated for treatment of prostate cancer as well. Therefore, our present invention is expected to minimize the treatment by surgery or chemotherapy.

*Curcuma mangga* Val. et Zipp., with the local name temu mangga, is a family of Zingiberaceae, and known as one of the spices and native medicinal plants from Southeast Asia. The plants then spread to Indonesia, Indo-Malaysia, Australia, and even Africa. Almost every Indonesian and Asian has ever consumed the spice plant, mainly as seasoning. Surprisingly the inventors of the present invention found that the extract of *Curcuma mangga* Val. et Zipp. can be used to treat prostate problems. Prior to this invention, there has not been any study describing the use or the benefit of *Curcuma mangga* Val. et Zipp. extract to overcome prostate problems, including prostate enlargement, as described in the present invention.

Out of various literatures that we previously studied, none mentioned the benefit of *Curcuma mangga* Val. Et Zipp. extract for BPH and prostate cancer treatment. Malek et. al. (2011) stated benefits of metanol extract from *Curcuma mangga* Val. Et Zipp. herbs (and the fractions thereof) in killing breast cancer cells (MCF-7), nasopharyngeal cancer cells (KB), lung cancer cells (A5A9), cervix cancer cells (Ca Ski), colon cancer cells (HT-29 and HCT 116), and human fibroblast cells (MRC-5). Rumiyati et. al. (2007) showed the benefit of essential oil from *Curcuma mangga* Val. Et Zipp. as an inhibitor of red blood cells (Raji cell line). The studies by Tedjo et. al. (2005) showed the benefit of chemoprevention of *Curcuma mangga* Val. Et Zipp. extract as an antioxidant in Chang cells.

The object of this invention is to disclose the potential use of natural ingredients to enrich the concept or theory that support the development of sciences, especially in health area. Moreover, it can provide a useful option, both in terms of preparation and processing practice of preparing a dosage form that is more practical in the use of *Curcuma mangga* Val. et Zipp. in health area, especially in treating prostate enlargement, by the extraction of the bioactive fractions.

BRIEF DESCRIPTION OF THE INVENTION

The objects and/or the solutions that are taught from the present invention will be explained in the preferred embodiments. The embodiments illustrated serve the purpose of understanding of this invention, without limiting the possibilities of other embodiments in variations and/or combinations and/or other modifications that can be learned from the practice of the present invention. The objects and/or the solutions that are taught in the present invention will be realized from elements and combinations which are described in the claims herein.

To achieve the solutions of the present invention, as explained in the embodiments and extensively described in this application, the first aspect of the present invention is directed to a preparation containing *Curcuma mangga* Val. et Zipp. extract or fractions or compounds derived thereof, as a single active ingredient or in a combination, in an amount or effective dosage for prevention, treatment or therapy of prostate enlargement. Furthermore, the preparations containing *Curcuma mangga* Val. et Zipp. extract that referred to the first aspect in the present invention could be used for prostate cancer therapy. The preparations according to the present invention also contain excipient or additive substances that are pharmaceutically acceptable and physiologically feasible.

Second aspect of the present invention is directed to preparations containing *Curcuma mangga* Val. et Zipp. extract which functions as an inhibitor of the formation of 5-alpha-reductase enzyme.

Third aspect of the present invention is directed to preparations containing *Curcuma mangga* Val. et Zipp. extract which functions as an inhibitor of the formation of androgen receptor.

BRIEF DESCRIPTION OF THE DRAWINGS

The following drawings, which are incorporated in and constitute a part of the present application, illustrate one or several embodiments of the invention. The following drawings serve to explain the principles which are taught by the present invention.

FIG. 1 shows Thin Layer Chromatography (TLC) profile of *Curcuma mangga* Val. et Zipp. extract.
  a. *Curcuma mangga* Val. et Zipp extract in methanol
  b. *Curcuma mangga* Val. et Zipp extract in ethanol 70%
  c. *Curcuma mangga* Val. et Zipp extract in ethanol 96%
FIG. 1A. Observations at 254 nm UV light
FIG. 1B. Observations at 366 nm UV light
FIG. 1C. Observations at visible light
FIG. 1D. Observations at 366 nm UV light after sprayed with $H_2SO_4$ 10%
FIG. 1E. Observations at visible light after sprayed with $H_2SO_4$ 10%
FIG. 2 shows the effect of *Curcuma mangga* Val. et Zipp. extract against PC3 cells proliferation.
FIG. 3 shows the effect of *Curcuma mangga* Val. et Zipp. extract against A549 cells proliferation.
FIG. 4 shows result of FACS experiment a.) Control treatment b.) Treatment with extract of *Curcuma mangga* Val. et Zipp. 50 µg/ml c.) Treatment with extract of *Curcuma mangga* Val. et Zipp. 100 µg/ml d.) Treatment with extract of *Curcuma mangga* Val. et Zipp. 150 µg/ml.
FIG. 5 shows qPCR results of 5-alpha-reductase-1 genes in PC3 cells after the administration of *Curcuma mangga* Val. et Zipp. extract.
FIG. 6 shows qPCR results of androgen receptor genes in PC3 cells after the administration of *Curcuma mangga* Val. et Zipp. extract.
FIG. 7 shows qPCR results of PI3 Kinase genes in PC3 cells after the administration of *Curcuma mangga* Val. et Zipp. extract.
FIG. 8 shows Western Blot results of 5-alpha-reductase-1 in PC3 cells after the administration of *Curcuma mangga* Val. et Zipp. extract.
FIG. 9 shows Western Blot results of Dihydrotestosterone (DHT) in PC3 cells after the administration of *Curcuma mangga* Val. et Zipp. extract.
FIG. 10 shows the effect of *Curcuma mangga* Val. et Zipp. extract against the levels of DHT.
FIG. 11 shows the results of *Curcuma mangga* Val. et Zipp. extract administration to rats that had experienced prostate gland enlargement.
  a.) Rats from sham-operated (normal) group
  b.) Rats from negative control group
  c.) Rats from group that treated with *Curcuma mangga* Val. et Zipp. extract 92.37 mg/kg body weight
  d.) Rats from group that treated with *Curcuma mangga* Val. et Zipp. extract 184.74 mg/kg body weight
  e.) Rats from positive control group (Finasteride 1 mg/kg body weight)
FIG. 12 shows graphic of the percentage of seminal vesicle weight development of rats as experimental animals.
FIG. 13 shows graphic of DHT plasma concentrations (pg/mL) of each experimental animals group.
FIG. 14 shows graphic of LH plasma concentrations (pg/mL) of each experimental animals group.

BRIEF DESCRIPTION OF THE TABLES

The following tables are incorporated in and constitute a part of the specification of the present application, illustrate one or several embodiments of the invention. The following tables serve to explain the principles which are taught by the present invention.

Table 1 shows the decreasing fold of genes expressions associated with DHT pathways.

Table 2 shows the decreasing fold of genes expressions associated with PI3/Akt and MAPK pathways.

Table 3 shows genes that experienced the highest increase of genes expressions.

Table 4 shows genes that experienced the lowest decrease of genes expressions.

DETAILED DESCRIPTION OF THE INVENTION

The present invention will be discussed in details by giving examples without limiting the scope of the invention to the examples described.

A. EXTRACTION PROCESS OF *CURCUMA MANGGA* VAL. ET ZIPP

The present invention teaches an extraction process of *Curcuma mangga* Val. et Zipp. resulting in an extract that has utility in treating prostate gland enlargement. *Curcuma mangga* Val. et Zipp. is usually cultivated on the lowland up to altitude of 1000 m above sea level (Gusmaini et. al., 2004). Plants with the purpose as an anti-prostatic hyperplasia in accordance with the present invention were harvested between 8-12 months, when the parts of the plants above the soil have begun to turn yellow and dry out.

In the present invention, most preferred part of the plant of *Curcuma mangga* Val. et Zipp. is the rhizome. The research of rhizomes were conducted on the basis that the secondary metabolites that have bioactivity, more commonly found in the rhizome, while the other parts of the plants at the harvest time were considered as waste. However, the other parts of the plant should not be ruled out from the possibilities that they have the bioactivity that can be observed as well in the future.

The rhizome for raw materials are cleaned up first, the roots, the base and impurities are removed, and subsequently the raw materials are washed with water and drained. Thereafter, raw materials are air-dried and chopped to the length of 3-7 mm, and dried to obtain water content ≤13%. The length of chopped raw materials is selected to such an extent to obtain optimal extraction results. If the slice is too small, it will contain fine particles that can impede the filtering process. Meanwhile, if the slice is too big, it could disrupt the dissolution of constituent(s) from inside matrix of raw materials. Certain length of raw materials needs to be determined in order to expand the surface area, thus the contact area during the extraction process becomes wider and more effective in extracting bioactive constituent(s) contained in the raw materials.

After the chopping process was done, the materials are weighted and placed in an extractor, followed by maceration process and/or percolation using organic solvent(s) with ratio of (1:6)-(1-10) w/v, for 30-240 minutes at a temperature range of 30°-50° C.

Since bioactive constituent(s) in *Curcuma mangga* Val. et Zipp. shows the properties of semi-polar and non-polar which is soluble in non-water organic solvents that are semi-polar to non-polar, the use of organic solvent(s) in the present invention includes but not limited to methanol, ethanol, methylene chloride, chloroform, petroleum ether, and acetone.

Extraction process was continued with concentrating the micella through an evaporation process at a temperature range of 50σ-60° C. and a pressure range between 175-875 mbar until a concentrate is formed. The concentrate obtained was added with fillers including betacyclodextrin, corn starch, and aerosil, and dried using an oven at a temperature range of 60°-70° C. for 24-48 hours, and the results were milled. The yield of extract obtained in the present invention is about ±2-7%. The following examples of extraction process are carried out.

Example 1

9.1 kg of raw material is cut to a length of 3-7 mm, weighed and placed in an extractor, and added with methanol with ratio (1:9) b/v, and then maceration is conducted for 180 minutes. The addition of methanol solvent at ratio and maceration time that mentioned before is to ensure all of bioactive constituent(s) that have expected bioactivity can be optimally extracted into the liquid extract. After that, the result is filtered until the micella was obtained, and subsequently with micella concentrated through evaporation process at temperature 60° C. and pressure 337 mbar until a thick concentrate, brown, and aromatic smell is obtained. To obtain dry extract mass, then filler is added to the concentrate and dried using an oven at temperature 60° C. for 48 hours. Subsequently, the dry extract is milled. Yield of methanol extract that is obtained through the extraction process according to the present invention is about ±7%.

Example 2

60 kg of raw material is chopped to a length of 3-7 mm, weighed, and placed in an extractor, and added with ethanol 70% with ratio (1:8) w/v. Subsequently, maceration process is conducted for 30 minutes and percolation for 90 minutes at temperature 50° C. The result is filtered until micelle was obtained, followed by concentrated through evaporation process at temperature 60° C. and pressure 866.593 mbar until an extract concentrate is formed which is a liquid with brownish yellow and smells aromatic. Filler is added to the extract concentrate. The extract concentrate with the filler is then dried using an oven at temperature 60° C., for 46 hours. The yield of ethanol extract obtained according to the present invention is about ±4%.

Slightly different from the use of methanol as a solvent in the extraction process, the use of ethanol in the concentration of 70-96% and raw material/solvent ratio of (1:6)-(1:10) w/v, and the duration of maceration as well as percolation at specified temperature range, can optimally extract expected bioactive constituent(s) into micella liquid.

The use of ethanol in the present invention is more advantageous, both from economic aspect, which covers production costs related to the duration of maceration and percolation, and from safety aspect of the workers and environment. To obtain an extract which contains optimal bioactive constituent(s) according to the present invention, the extraction process is preferably conducted at a temperature range of 30°-50° C. More preferably, the extraction process is done at temperature 50° C., because it produces higher yield. The use of temperature above 50° C. is not suggested due to the flammable nature of ethanol.

The extraction process could be conducted using ethanol at the concentration of 70-96%. However, extraction using ethanol 70% is preferred because the extracted constituent in the production process is easier to be collected and not much residue left. The optimal yield obtained using ethanol 70% is ±6.2%. This yield is higher, thus more economical, if compared with the yield obtained from extraction process using ethanol at the concentration above 70%.

Other extraction process can be conducted with liquid-liquid extraction. The basic principle of liquid-liquid extraction is the partition of a solute between two immiscible solvents. The extraction process of *Curcuma mangga* Val. et Zipp. according to the teaching of the present invention could be continued with a liquid-liquid extraction method.

The concentrate obtained through extraction process above was further given an equal amount of additional water, and liquid-liquid extraction was performed using organic solvent including hexane, ethyl acetate, chloroform, and dichloromethane. Subsequently, the water and organic phase was separated, followed by concentrating the organic phase through evaporation at low pressure until an extract concentrate was obtained.

In the extraction process, filler addition is better to be conducted by mixing the filler suspension in the water first, approximately at the equal volume with the micella. Furthermore, filler suspension is added to the extract concentrate and homogenized by re-circulated and re-concentrated until 30-50% of the original volume was reached. The step of mixing the filler on the process of concentrating the extract is better, because the addition of filler can trap the active components that are non-polar, thus the adhesions of the active components to the machine could be reduced. In accordance to the present invention, in order to obtain the mass of dry extract, the fillers which are added into the concentrate includes betacyclodextrin, corn starch, and aerosil. The selection of betacyclodextrin as a filler is because its molecule is shaped like a "basket" that has a polar and non-polar properties, thus it can "wrap" the non-polar components from *Curcuma mangga* Val. et Zipp constituents. Moreover, the porous nature of aerosil which can absorb non-polar components of the essential oils (which are thought to contain the bioactive components) into the pores, thus help to increase the capacity of main fillers of corn starch in drying the extract of *Curcuma mangga* Val. et Zipp. The drying process is conducted for 24-48 hours to obtain the mass of dry extract. During the drying process of the mixture of extract and fillers, the temperature is set in the range of 60°-70° C. The temperature setting is made in such a way to preserve the active constituents and prevent the possibilities of alteration or damage of the active constituents in the extract caused by heat during the process. Further, the process is followed by grinding the dried extract.

*Curcuma mangga* Val. et Zipp that was obtained through the extraction process using methanol as the solvent has a bright yellow color with an aromatic odor and bitter taste. Meanwhile, *Curcuma mangga* Val. et Zipp that was obtained through the extraction process using ethanol as the solvent at the concentration of 70-96%, has a yellow to brownish yellow color with an aromatic odor and bitter taste. Methanolic extract is hardly soluble in water, whereas ethanolic extract is partly soluble in either water or ethanol. The percentages of loss on drying for both extracts were ≤5.00%.

Phytochemical tests were conducted to check the content of secondary metabolites contained in the extract of *Curcuma mangga* Val. et Zipp. Phytochemical tests were conducted to reveal the presence of alkaloids, saponins, phenols, flavonoids, terpenoids, and steroids. Meanwhile, the test for terpenoids and steroids group was also performed by TLC.

Alkaloids test was performed using Bouchardat LP reagent. LP Bouchardat reagent was prepared by dissolving 2 grams of iodium and 4 grams of potassium iodide in water until a final volume of 100 ml was reached. The test was performed by weighing 500 mg of extract, and then 9 ml water and 1 ml HCl 2 N were added to the extract. This solution was heated at the temperature of 95° C. for 5 minutes, and then was allowed to stand at room temperature and filtered. A total of 6 drops of filtrate were taken and was added with 4 drops of Bouchardat LP reagent. Positive reaction to the alkaloid is if brown to black precipitate formed. The results of alkaloid test against *Curcuma mangga* Val. et Zipp extract showed that there was no formation of precipitate, thus the extract was stated negative against alkaloid test.

Phytochemical test against saponin group was performed by weighing 500 mg of extract and given additional 10 ml of boiling water, shaken vigorously for 10 seconds, and then allowed to stand for 10 minutes. The solution was added with 1 drop of 2 N HCl and observed. Positive reaction against saponin test is occurred if foam appears and the foam persists after the addition of 2 N HCl. *Curcuma mangga* Val. et Zipp showed a positive reaction against saponin due to the foam that persists after the addition of 2 N HCl.

Flavonoid test was performed by weighing 500 mg of extracts, and then added with 10 ml of methanol and refluxed for 10 minutes. While still hot, the solution was filtered. The filtrate was diluted with 10 ml of water. Once cool, 5 ml of petroleum ether was added to the solution, and then the solution was shaken and allowed to stand. Methanol-water layer was collected and dried using an evaporator. The rest of dried extract was dissolved using 5 ml ethyl acetate and filtered. Furthermore, as many as 1 ml of the filtrate was taken, inserted into a test tube, and evaporated again until dry. Subsequently, as many as 1 ml of 95% ethanol, 0.1 gram of Mg powder, and 1 ml of hydrochloric acid was added slowly. If yellow, orange, and/or red-purple color was formed, then it showed a positive reaction against flavonoid. Flavonoid test of the extract of *Curcuma mangga* Val. et Zipp was positive, which was indicated by the formation of concentrated orange solution.

Phenol test was performed by weighing 500 g of extract and the extract was inserted into a test tube and then 20 ml of water was added to the tube and boiled. The solution was filtered while it was still hot, and the filtrate was taken and dropped into watch glass. Furthermore, several drops of iron (III) chloride solution was added to the filtrate and if it formed a dark green, blue, and/or purple solution, then it showed a positive reaction against phenol. From the results of this test, the extract of *Curcuma mangga* Val. et Zipp was stated positive against phenols test due to the formation of green solution.

Terpenoids and steroids test was performed by weighing 500 mg of extract and dissolved in 2 ml of chloroform, and then filtered. The resulting filtrate was subsequently transferred into a drop plate and allowed to stand until the solvent evaporated. Thereafter, Liebermann-Burchard reagent was added (1 drop of concentrated sulfuric acid and 3 drops of acetic acid anhydrate). If red, pink, and/or purple colors appeared, then it showed a positive reaction against terpenoid and or steroid. A positive result was showed by the terpenoid and steroid tests against *Curcuma mangga* Val. et Zipp extract by the onset of red color.

TLC test of the extract was performed using 10 mg of sample dissolved in 1 ml of absolute ethanol, and then 25 µL of sample was spotted on silica gel 60 F254 plate. An elution on an 8 cm pathway was performed using n-hexane and ethyl acetate (5:1) solvent, and then the spots were observed under 254 nm and 366 nm UV light and visible light (FIG. 1). FIG. 1A is the result of the plate observation under 254 nm UV light, it showed a positive spots at Rf 0.20, 0.29, and 0.80. Observation under 366 nm UV light as in FIG. 1B, showed the fluorescent blue spot at Rf±0.26, 0.34, and 0.42, as well as blue spot at Rf±0.53. FIG. 1C is the result of plate observation under visible light which showed no spots. The TLC plates were further sprayed with 10% of $H_2SO_4$ in the water, and then heated at temperature 150° C., and was observed under 366 nm UV light, light brown spot appeared at Rf±0.29, blue spots at Rf±0.47 and 0.83, and yellow spot at Rf±0.91 (FIG. 1D). Meanwhile, when the plates were observed under visible light, brownish purple spots at Rf±0.31 and light brown spot at Rf±0.60 appeared, which showed a positive reaction against terpenoid and steroid (FIG. 1E).

According to the phytochemical tests above, the extract showed a positive reaction against flavonoids, saponins, phenols, terpenoids, and steroids, but showed a negative reaction against alkaloids. Meanwhile, the results of TLC analysis also showed that the extract of *Curcuma mangga* Val. et Zipp contains steroids and terpenoids.

The results of phytochemical test and TLC on ethanolic and methanolic extract of *Curcuma mangga* Val. et Zipp confirmed that the active spots that appeared were the group of terpenoids and steroids.

B. *CURCUMA MANGGA* VAL. ET ZIPP. EXTRACT AS A PC3 CELL GROWTH INHIBITOR AND PC3 CELL DEATH INDUCER

Method

Cell Culture and Treatment Administration of *Curcuma mangga* Val. et Zipp.

Prostate cells used in the present invention are human prostate cancer cells (PC3). In addition, human lung cancer (A549) cells were also being used as an additional supporting data of cell viability. Cells were cultured using serum-containing medium in an incubator with temperature of 37° C. and CO2 at the concentration of 5% until 80% of surface of flask covered by cells. Further, cells were transferred into 96 well-plates using a medium without serum, and were incubated with the same conditions for 24 hours. The treatment in the form of extracts of *Curcuma mangga* Val. et Zipp. with concentrations ranging from 25 µg/ml to 200 µg/ml was given to the cells and further re-incubated with similar conditions for 24 hours. These cells culture method were applicable to all tests related to the inhibitory activity of *Curcuma mangga* Val. et Zipp. extract against the formation of enzyme 5-alpha-reductase-1 and androgen receptor, as well as microarray analysis.

Cell Viability Test Using MTT Test (3-(4,5-dimethylti-azol-2-il)-2,5-diphenyltetrazolium bromide))

Cell viability was determined using MTT test in accordance with the instructions from the manufacturer. The results of MTT test were converted using standard curve of PC3 cells, thus the number of viable and dead cells were obtained. Those numbers then were used to measure IC50 (the values that can shows the concentration of a sample required to induce 50% cell death from the whole population) using Biostat statistic software.

Besides PC3 cells, MTT test were also carried out on lung cancer (A549) cells as an additional data about *Curcuma mangga* Val. et Zipp activities against cells growth inhibition. The performed method on A549 cells was similar to PC3 cells method.

The Use of FACS to Observe PC3 Cell Cycle

After treatment with *Curcuma mangga* Val. et Zipp., cells were fixated prior to analyzing by FACS machine. The cells fixation was performed by cell-washing process using phosphate buffer saline (PBS) and precipitation of the materials contained in the treatment medium. Cells and precipitated materials were incubated in 70% ethanol 70% at temperature of 4° C. for 24 hours. Furthermore, cells were colored using propidium iodide and analyzed using FACS BD machine.

Result

The result of MTT test showed a decreasing number of cells with increasing concentrations of the extract (FIG. 2). The number of IC50 obtained for *Curcuma mangga* Val. et Zipp extract against PC3 cells were 92.60-127.45 µg/ml. The capability of cell growth inhibition was also seen in A549 cells, with the IC50 obtained between 39.07-42.59 µg/ml (FIG. 3). The result of FACS experiment showed that after the treatment with the extract of *Curcuma mangga* Val. et Zipp. there was a change in cell cycle compared to control (FIG. 4). The percentage of G0 cycle was increased, meanwhile the cycle of G, S, and G2/M was decreased with increasing concentrations of *Curcuma mangga* Val. et Zipp. extracts that were given.

Discussion

The result of MTT test showed that *Curcuma mangga* Val. et Zipp. has the capability to inhibit the PC3 cell growth. The capability can be seen from the decreasing number of PC3 cells with increasing concentrations of *Curcuma mangga* Val. et Zipp. extract that were given. The decrease begun to occur at the concentration of 50 µg/ml until the concentration of 200 µg/ml, and the IC50 about 92.60 to 127.45 µg/ml. Cell growth inhibition processes was also seen in A549 cells. The inhibition started at the concentration of 25 µg/ml and continues to decrease until the concentration of 75 µg/ml with IC50 about 39.07 until 42.59 µg/ml. According to the data that was obtained, it can be seen that *Curcuma mangga* Val. et Zipp. extract can be used as an inhibitor of PC3 cell growth, as well as inhibitor of A549 cell growth.

The result of FACS experiment showed the increasing number of cells at G0 phase with increasing concentrations of *Curcuma mangga* Val. et Zipp. extract that was given. G0 phase showed the occurrence of apoptosis and cells death. The increase in the number of cells at the cycle shows the inhibition of PC3 cell growth through the induction of cell death. The result was strengthened by the data that there were decreases in cell cycle G, S, and G2/M with increasing concentrations of *Curcuma mangga* Val. et Zipp. extract. Those cycles are the signs of cell division activities, thus if those cell cycles were decreasing, it shows a decreasing cell growth (Reynolds & Schecker 1995: 64; Nunez 2001: 67).

The capability of *Curcuma mangga* Val. et Zipp. extract to inhibit prostate cancer cells growth, is useful to overcome prostate problem in men, including BPH and prostate cancer. The inhibition of cells growth can stop the velocity of uncontrolled cells growth, meanwhile in BPH, it can reduce the enlargement. This extract also can be developed to inhibit lung cancer cells growth.

Conclusion

According to the results obtained in the MTT test and FACS, it can be concluded that *Curcuma mangga* Val. et Zipp. extract has the capability to inhibit the prostate cancer cells growth and to induce PC3 cells death. It can be seen from the decreasing number of cells with increasing concentrations of *Curcuma mangga* Val. et Zipp. extracts that was given.

C. *CURCUMA MANGGA* VAL. ET ZIPP. EXTRACT IS CAPABLE TO INHIBIT THE FORMATION AND DECREASE THE ACTIVITY OF DHT THROUGH DECREASING 5-ALPHA-REDUCTASE-1 AND ANDROGEN RECEPTOR EXPRESSIONS

Method

RNA Isolation and Real Time PCR (qPCR)

The total of RNA was isolated from cells after 24 hours treatment using TRIzol reagent. The isolation was performed following the instructions from TRIzol manufacturer. Furthermore, the concentration of the total RNA was calculated using Nano Drop tools based on the isolation results.

RNA that was obtained, further being a template to do rt-PCR. The DNA that was resulted from rt-PCR subsequently was used as a template to do qPCR. qPCR process was performed using master mix iQ SYBR and specific primers of 5-alpha-reductase-1, androgen receptor, and PI3 kinase. The conditions for qPCR were an optimization results based on the previous experiments.

Protein Isolation and Western Blot 5-alpha-reductase-1 and DHT

Total protein was isolated after 24 hours treatment with the extract of *Curcuma mangga* Val. et Zipp. The isolation was performed using Lysis Buffer and TRIzol method. The result of total protein isolation further was calculated using Lowry method. Protein that was obtained subsequently was used as a sample for Western Blot against 5-alpha-reductase and DHT, and the DHT test using Elisa kit Alpha Diagnostic International. The analytical process of semi-Western Blot was performed in accordance to the general method, which is using specific antibody for 5-alpha-reductase-1 and DHT. The detection of Western Blot was performed using HRP-conjugated (Horseradish Peroxidase) secondary antibody and coloring with luminol.

Quantitative analysis was performed using Elisa kit in accordance to the protocol provided by the manufacturer. PC3 cells that were used in this present invention was treated with excessive testosterone which is 8.8 µg/ml, and was treated with 150 µg/ml *Curcuma mangga* Val. et Zipp extract and 2 µg/ml finasteride, in separate groups. In this present invention, the finasteride treatment group was a positive control.

Result qPCR result showed a decreasing 5-alpha-reductase-1 gene expressions, androgen receptor gene, and PI3 kinase gene (FIGS. 5, 6, and 7). The decreasing has started at concentration 50 µg/ml and continues to decrease until concentration 150 µg/ml. The Western Blot result showed that the administration of *Curcuma mangga* Val. et Zipp. extract causes a decreasing protein expression of 5-alpha-reductase-1 (FIG. 8), and consequently the DHT levels was also decreased (FIG. 9).

The similar results also occurred in the quantification with Elisa kit. PC3 cells were treated with excessive testosterone to observe the changes in DHT levels. PC3 cells with excessive testosterone, showed higher DHT production than the control cells. Cells that were treated with excessive testosterone and *Curcuma mangga* Val. et Zipp. extract, resulted in reduced levels of DHT similar with the cells that were treated with excessive testosterone and finasteride (FIG. 10).

Discussion 5-alpha-reductase is an enzyme that plays a role in the conversion of androgen testosterone to DHT. One of the functions of the androgen is in the division of prostate cancer cell. 5-alpha-reductase has 2 isozymes: type-1 and type-2. Those two isozymes are different in optimum pH and coding genes. The levels of gene expressions are also different. Type 1 and 2 are more expressed in BPH conditions than a normal, meanwhile in prostate cancer condition, only type-1 that is more expressed than a normal (Smith et al. 1998: 1361; Soderstrom et al. 2001: 855; Schmidt et al. 2004: 944). Since BPH and prostate cancer are the diseases within the scope of this present invention, only 5-alpha-reductase-1 that was used as the parameter.

Testosterone will be converted into DHT by 5-alpha-reductase-1 enzyme, which then binding to androgen receptor and activate the regulation of prostate cancer cell growth (Soderstrom et al. 2001: 855; Asada et al. 2001: 2875). The experiment result showed a decreasing gene expression of 5-alpha-reductase-1 in qPCR analysis and decreasing numbers of expressed protein in Western Blot analysis. The decreasing gene expressions and protein numbers showed a decreasing numbers of 5-alpha-reductase-1 in prostate cancer cells after the administration of *Curcuma mangga* Val. et Zipp. extract. The decreasing number of 5-alpha-reductase-1 enzyme was also supported by the result that DHT level was reduced with increasing concentration of *Curcuma mangga* Val. et Zipp. extracts that was given. The decreasing number of 5-alpha-reductase-1 enzyme will lead to the decrease in the conversion of testosterone into DHT, thus DHT concentration in prostate cancer cell will be reduced. The decreasing concentration of DHT will cause a decreasing growth regulation of prostate cancer cell due to reduced binding of DHT to the androgen receptor. It can lead to the decreasing growth of prostate cancer cell which is consistent with the previous experiment results (MTT dan FACS).

The experiment result also showed a decreasing gene expression of androgen receptor in qPCR analysis, which is showed by the decreasing number of androgen receptors in prostate cancer cells. The previous experiment results showed that the inhibition of prostate cancer cell growth was occurred due to the decreasing concentration of DHT, while this experiment results showed that the inhibition of the cell growth was also occurred due to the inhibition of DHT binding to the androgen receptor. The decreasing number of androgen receptors will also cause a reduced binding of DHT to the receptor, which in the end leads to the decreasing growth regulation of prostate cancer cell.

The decreasing gene expressions of 5-alpha-reductase and androgen receptor are related with PI3/Akt pathway. Those two genes are regulated through PI3/Akt pathway. PI3 kinase is an enzyme that plays a role in regulating cellular functions, including in the development of male sexual character and phenotype. The experiment results showed that the treatment of *mangga* Val. et Zipp. extract in PC3 cells could decrease the numbers of PI3 kinase in mRNA levels. The decrease will affect the regulation of Akt phosphorylation which subsequently affecting the activation of another transcription factors which results in the decreasing transcription of 5-alpha-reductase and androgen receptor. As has been discussed previously, the decreasing expression of those two genes can decrease prostate cancer cell growth.

Conclusion

The decreasing gene expression of 5-alpha-reductase-1 and androgen receptor showed the capability of *Curcuma mangga* Val. et Zipp. extract in treating either BPH or prostate cancer through the inhibition of prostate cancer cell growth. The decrease in 5-alpha-reductase-1 gene expressions will inhibit prostate cancer cells growth through decreasing concentration of DHT required by prostate cancer cells to activate the regulation of prostate cancer cells growth. Through decreasing the activation zone in the process of prostate cancer cells growth, the decrease in the expressions of androgen receptor inhibited the growth of prostate cancer cells. The decrease in the expressions of those two genes which impact to a decreasing concentration of DHT has caused the inhibition in the regulation of prostate cancer cells growth.

D. MICROARRAY ANALYSIS AS SUPPORTING DATA OF *CURCUMA MANGGA* VAL. ET ZIPP. EXTRACT

Method

RNA Isolation and Microarray Analysis

RNA total were isolated from the cells after 24 hours treatment using TRIzol reagent. The isolation was performed following the instructions from TRIzol manufacturer. Furthermore, the concentration of the total RNA was calculated using spectrophotometer (Bio Spec Mini, Shimadzu), meanwhile to measure the quality aspects, Agilent Bio Analyzer was used. The RNA was subsequently processed according to the protocol recommended by Affymetrix and Nu Gen. Briefly, a total of 100 ng of RNA total was reverse-transcripted to produce cDNA hybrid that will be used as a template for producing a double-stranded cDNA with a unique DNA/RNA heteroduplex at one end. Afterwards, the amplification process was performed with Single Primer Isothermal Amplification (SPIA) that will produce a single-stranded antisense DNA. cDNA that was resulted from SPIA modification was fragmented and labeled with biotin and was hybridized into Affymetrix Human Gene 1.0 ST Arrays for 18 hours with a temperature 45° C. and 60 rpm rotation. Subsequently, the Arrays were washed and colored according to the FS 450_0007 protocol and were scanned using Affymetrix 3000 76 scanner. The data that was obtained, was analyzed using Partek® Express™, thus the changes in gene expressions were known. The changes in gene expressions were sorted from the highest to the lowest, and the 50 highest and lowest genes were taken. Subsequently, those genes were sorted, selected, and analyzed to discover the correlation between the genes and the pathways. Sorting, selection, and analysis of genes were performed using Reactome (www.reactome.com).

Result

Microarray results showed that the expression of the genes such as 5-alpha-reductase-1 or 2 and androgen receptor, which are genes related to prostate growth, have decreasing folds (Table 1).

TABLE 1

Decreasing folds of genes expressions associated with DHT pathways

| Gene | Fold |
| --- | --- |
| 5-alpha-reductase-2 | −1.12 |
| androgen receptor | −1.03 |

Moreover, the microarray results also revealed that the expressions of the genes related to MAPK mechanism pathways also have decreasing folds. Those genes are Epidermal Growth Factor (GF), Epidermal Growth Factor Receptor (GFR), Phosphoinositide-3-Kinase (PI3K), v-Ha-Ras Harvey rat sarcoma viral oncogene homolog (RAS), v-raf murine sarcoma 3611 viral oncogene homolog (RAF), v-akt murine thyoma viral oncogene homolog 3 (Akt), and mitogen-activated protein kinase kinase (MEK) (Table 2).

TABLE 2

Decreasing fold of genes expressions associated with PI3/Akt and MAPK pathways

| Genes | Fold |
| --- | --- |
| GF | −1.71 |
| GFR | −1.11 |
| PI3 | −1.01 |
| Akt | −1.29 |
| RAS | −1.04 |
| RAF | −1.33 |
| MEK | −1.17 |

When the microarray results were sorted from the highest increasing fold until the lowest decreasing fold, and then were taken per 50 genes, sorted, and analyzed using Reactome, it showed different pathways as the indication for another diseases (Table 3 and 4).

TABLE 3

Genes that experienced the highest increasing gene expressions

| No | Gene Symbol |
| --- | --- |
| 1 | NPY1R |
| 2 | RGS2 |
| 3 | CSRNP3 |
| 4 | SPINT4 |
| 5 | RPE65 |
| 6 | TRERF1 |
| 7 | HOXB13 |
| 8 | BLID |
| 9 | CCDC141 |
| 10 | TLL1 |
| 11 | SLC26A5 |
| 12 | TMEM19 |
| 13 | WDR52 |
| 14 | GLI3 |
| 15 | WDR52 |
| 16 | NET1 |
| 17 | ZNF737 |
| 18 | ZNF302 |
| 19 | C5orf13 |
| 20 | F2RL1 |
| 21 | NAIP |
| 22 | FJX1 |
| 23 | MGAT5 |
| 24 | SPRY4 |
| 25 | PLD1 |
| 26 | FRK |

TABLE 3-continued

Genes that experienced the highest increasing gene expressions

| No | Gene Symbol |
| --- | --- |
| 27 | GBA2 |
| 28 | SLC14A1 |
| 29 | ANKRD36B |
| 30 | SLCO1C1 |
| 31 | RIN2 |
| 32 | NAIP |
| 33 | SPARC |
| 34 | C5orf54 |
| 35 | TAS2R10 |
| 36 | NAPEPLD |
| 37 | NCOA5 |
| 38 | MEGF8 |
| 39 | SKP2 |
| 40 | ANKRD36B |
| 41 | MAT2A |
| 42 | SHISA3 |
| 43 | TRIB2 |
| 44 | ZNF75A |
| 45 | SIDT1 |
| 46 | ANKRD36 |
| 47 | C14orf39 |
| 48 | GALNT7 |
| 49 | BIVM |
| 50 | EHF |

TABLE 4

Genes that experienced the lowest decreasing gene expressions

| No | Simbol Gen |
| --- | --- |
| 1 | HMOX1 |
| 2 | DDIT3 |
| 3 | IL8 |
| 4 | GPCPD1 |
| 5 | GCOM1 |
| 6 | SC4MOL |
| 7 | CDC6 |
| 8 | EPGN |
| 9 | DHRS9 |
| 10 | ZFP36 |
| 11 | NFIL3 |
| 12 | DUSP1 |
| 13 | TM4SF19 |
| 14 | PLIN2 |
| 15 | RNF19B |
| 16 | ANXA10 |
| 17 | PIM1 |
| 18 | DYRK3 |
| 19 | HIVEP1 |
| 20 | HGF |
| 21 | STK32A |
| 22 | PPP1R15A |
| 23 | PIR |
| 24 | INSIG1 |
| 25 | RND3 |
| 26 | TMEM159 |
| 27 | GCNT3 |
| 28 | HMGCS1 |
| 29 | CXCL2 |
| 30 | DTL |
| 31 | HIST2H2BF |
| 32 | GK |
| 33 | FAM102A |
| 34 | ATF3 |
| 35 | HIST2H2BF |
| 36 | IL24 |
| 37 | SLFN11 |
| 38 | DNAJB1 |
| 39 | UGDH |
| 40 | MND1 |

TABLE 4-continued

Genes that experienced the lowest decreasing gene expressions

| No | Simbol Gen |
|---|---|
| 41 | IL6 |
| 42 | CPEB2 |
| 43 | CTH |
| 44 | HSPA1B |
| 45 | UPP1 |
| 46 | JMY |
| 47 | AREG |
| 48 | TIFA |
| 49 | HIST2H2BE |
| 50 | GCLC |

Discussion

Microarray results have strengthened the indication that the prostate cancer cells growth was inhibited through DHT inhibition pathway. According to the microarray results, the expression of the gene encoding for 5-alpha-reductase-2 (isozyme of 5-alpha-reductase-1) and androgen receptor were decreased. Microarray results also strengthened the indication that the prostate cancer cells growth was inhibited through PI3 kinase and Akt inhibition pathways due to the decrease in the gene expressions of PI3 kinase and Akt. In addition, the gene expressions of MAPK pathways, which are still related to PI3/Akt pathways, were also decreased.

Indications for the treatment of other diseases were also seen from the microarray results. Reactom analysis results from sequencing of 50 genes that up-regulated showed that there was changes in the gene expressions associated with G Protein-Coupled Receptor (GPCR) pathways. These pathways can be related to immune system and hemostatic process. The analysis results for up-regulated genes also showed the effect of *Curcuma mangga* Val. et Zipp. extract against genes related to biological oxidation. Meanwhile, based on the 50 down-regulated genes, the majority of the genes that undergo expression changes were in the similar pathways. Several differences were occurred in the genes that were associated with cell cycles, diabetes, cholesterol, as well as lipid and lipoprotein metabolism. Besides its indication for the treatment of prostate disease, *Curcuma mangga* Val. et Zipp. extract was also indicated for the treatment of other diseases in which its genes are stated in Table 3 and 4.

Conclusion

Microarray results that were obtained further strengthens the indication that *Curcuma mangga* Val. Et Zipp. extract in accordance with the present invention can treat prostate disease (BPH and prostate cancer), through the changes in DHT, PI3/Akt, and MAPK pathways. In addition, based on the consideration of its effects against several genes regulation, the microarray results also revealed the possibility of using *Curcuma mangga* Val. et Zipp. extract in the treatment of another diseases, mainly for diseases that are related with GPCR, including immune system and hemostatic, cell cycle pathways, biological oxidation, diabetes, cholesterol, as well as lipid and lipoprotein metabolism.

E. THE INHIBITION OF PROSTATE GLAND GROWTH IN RATS

Method

Animal Breeding

Animals that were used in the present invention were male rats (*Rattus norvegicus*) Wistar strain weighing between 200-250 grams from Indoanilab, Bogor, Indonesia. The animals were bred in special cages, in groups, with a normal light setting, which are 12 hours of light and 12 hours of dark and received food and drinking water ad libitum.

The procedure of animals breeding followed the applicable rules that refer to the Guide for the care and use of Laboratory Animals, 8$^{th}$ edition. All procedures regarding the use of animals has been reviewed and approved by ethics committee of animals trial used with protocol number DOC-DLBS-BIOL-VVR-APC-015.

Animals Groups

The animals were divided into five groups: sham-operated group (normal group), negative control group that is BPH group without any treatment, positive control group that is treated with finasteride 1 mg/kg of body weight, and treatment group which divided into two groups based on the dose of *Curcuma mangga* Val. et Zipp. extract that they received, namely 92.37 mg/kg and 184.74 mg/kg of body weight. In all animals the growth of its prostate gland were induced, except for the animals in the sham-operated group.

The Induction of Prostate Gland Growth

Those rats were induced with subcutaneous administration of testosterone injection to stimulate the growth of prostate gland at the dose of 10 mg/kg body weight, every day for 7 days. The administration of testosterone injection was performed after the removal of testes (castration) and sham surgery in rats. The castration procedures were performed to avoid bias caused by the differences of testosterone amount produced by each individual rat.

All animals were anaesthesized prior to surgery. The anaesthesia was administered using the mixture of ketamine and azepromazine maleic at the dose of 75 mg/kg and 2.5 mg/kg of body weight respectively.

Treatment was given with collapsed dorsal animal position and was prepared according to the operation purposes. Incision was performed in the skin at prepubic area through linea alba. After incisions to the skin and subcutaneous area were performed, then the testis was found. The blood vessel above the testis and vas deferens was fastened using a 4/0 chromic gut. Subsequently, the peritoneal cavity was sutured using a 4/0 chromic gut and the skin was sutured using 4/0 silk.

After the surgery, antibiotics and analgesics were given to the rats to avoid bacterial infections and pain caused by the surgery. Flunixin was administered subcutaneously twice a day at dose 1.1-2.5 mg/kg of body weight as analgesic, and gentamicin was administered subcutaneously once a day at dose 5-8 mg/kg of body weight, as antibiotic to prevent secondary infections.

Result

FIG. 11 is a photo that was taken in the last week from each rat group. Anatomic pathology examination on negative control group found each bladder containing urine in significant amount. It was occurred because prostate that surrounds the vesica urinary, enlarged and clamping the way out of urine. As additional information, prostate is divided into two areas, namely ventral and retral area that surrounds the vesica urinary. Also because of the enlargement, at routine daily examination with palpation at lower abdominal, especially during the third week until the sixth week, it was frequently found hardening due to solids and water fluctuation.

Numerical data was obtained according to the weighing results of seminal vesicle and prostate that has been compared with the final weigh of animals. FIG. 12 showed a graph of organ weigh of each animal from each treatment, which the prostate size, depends on individual response from each animal, as well. With similar dosage and period of treatment, there were several individuals that significantly have bigger prostate and the others did not have big enough prostate.

Regarding DHT concentration in rats' plasma can be seen from FIG. 13. From the graphic, it was known that the administration of testosterone without medical treatment (placebo), resulting in increased levels of DHT. Meanwhile, treatment with finasteride 1 mg/kg and *Curcuma mangga* Val. et Zipp. extract at doses 92.37 mg/kg and 184.74 mg/kg body weight, can lead to the suppression of DHT plasma concentration.

Treatments of patient with prostate gland enlargement can be administered in several mechanisms, including alpha-blocker treatments, anti-androgen medicines, and another types of medicines which works by inhibiting the work of 5-alpha-reductase enzymes in conversion of testosterone into DHT.

Discussion

Based on the experiment, it turns out that the induction of prostate enlargement affects the plasma concentration levels of Luteinizing Hormone (LH) in rats, especially in BPH group. From FIG. 14, it can be seen that LH concentration was increased. The increase in LH concentration was occurred due to the process of androgen blockade in the prostate and pituitary. However, the treatment with *Curcuma mangga* Val. et Zipp. extract did not results in the significant increase of LH plasma concentration.

From several observations that were performed, treatment with *Curcuma mangga* Val. et Zipp. did not have influences in the concentration of LH that works as anti-androgen. However, the obtained data showed a result that asserting the mechanism of action of *Curcuma mangga* Val. et Zipp. extract in treating prostate diseases was similar with the mechanism of action of finasteride which is a 5-alpha-reductase enzyme inhibitor. It can be seen from the decreasing concentration of DHT that occurred after treatment with *Curcuma mangga* Val. et Zipp. extract and finasteride in rats that previously has been induced for prostate enlargement. This result strengthened the molecular data obtained previously.

The analysis of pathological anatomy results, DHT concentration and the comparison of prostate development with animals weight enables the use of *Curcuma mangga* Val. et Zipp. extract in the inhibition of prostate cancer formation through the inhibition of DHT, which is the most potent form of testosterone, in the development of prostate cancer.

F. PHARMACEUTICAL PREPARATION AND NUTRACEUTICALS

The present invention includes the pharmaceutical compositions and dosage forms that contains *Curcuma mangga* Val. et Zipp. extract in effective amount, as an active ingredient in one dosage herb and/or mixed herbs, including carrier, excipients or additives that are pharmaceutically acceptable and physiologically suitable.

In the process of preparing pharmaceutical composition as taught in the present invention, the active ingredient *Curcuma mangga* Val. et Zipp. extract can be mixed with, or dissolved in excipient(s), or contained in carrier that can be made in the form of capsule, sachet, paper, as well as other packaging materials. If pharmaceutically acceptable excipient is used as solvent, the excipient can be in form of solid, semi-solid or liquid (oral and injection), that acts as a carrier or medium for the active ingredient. Thus, pharmaceutical composition according to this invention can be made in the form of pill, capsule, tablet, powder, sachet, solution, syrup, emulsion, suspension, effervescence tablets, gel, ointment, cream, mouthwash, massage oil, suppository, or injection. In addition, pharmaceutical composition comprising *Curcuma mangga* Val. et Zipp. extract according to this invention can also be made as supplement, vitamin, as well as food and beverage production.

Composition according to the present invention can be formulated using methods that have been applied in pharmaceutical industry that causes the active ingredient to be released directly, sustained or controlled after the patient receives such dosage forms. Tablet or pill according to the present invention can be coated to extend the half-life of the extract thus its frequency of use can be reduced.

Method of formulating this composition in a solid form, such as tablet, can be done by mixing the active ingredient of the extract of *Curcuma mangga* Val. et Zipp., with excipient(s) to form an initial formulation containing homogenous mixture from the composition according to the present invention. The initial formulation is a mixture containing the active ingredient of the *Curcuma mangga* Val. et Zipp. dispersed homogenously, so it can be uniformly distributed to conform the proper dosage into forms such as, for example, capsule, tablet, or pill.

Additional protection coat may be applied to the tablet or pill according to the present invention to reduce or cover the bitter taste from the composition or the active ingredient *Curcuma mangga* Val. et Zipp. extract.

Extract of *Curcuma mangga* Val. et Zipp. in an effective amount or dosage according to the present invention is the dosage of the extract that can inhibit prostate cancer cells growth. An effective amount depends on the physical condition of the patient, including weight, age, and other factors; includes on type, size and number of prostate cancer cells and other targeted pathologies condition.

Liquid dosage forms such as herbal drinks formulation, can be prepared by mixing the active ingredient *Curcuma mangga* Val. et Zipp. extract with water and surfactant, for example hydroxypropylcellulose or other similar materials.

Some of the substances as explained previously in herbal drinks formulations is required for making herbal syrup preparation. However, for syrup preparation, other components, such as thickener substances, stabilizer substances are required. Semi-solid dosage forms, such as jelly, can be prepared by mixing the active ingredient *Curcuma mangga* Val. et Zipp. extract with certain hydrocolloid including gelatin, carrageenan, pectin, gum *arabicum*, guar gum, and other similar materials.

Herbal formulation in solid food preparation, such as biscuit, bread, and cookies, can be prepared using the active ingredient *Curcuma mangga* Val. et Zipp. extract as a component with important effect on body health. The preparation of solid food preparation such as biscuit, bread, and cookies according to this invention can be done using common preparation and other materials including butter, sugar, eggs, and other supporting materials.

This invention also anticipated the used of *Curcuma mangga* Val. et Zipp. extract as a therapy that performed in conjunction with or after radiation therapy.

This present invention also anticipated the used of *Curcuma mangga* Val. et Zipp. extract in conjunction with or as an additional in the composition of anti-BPH or other medical substances that available in market.

G. INDUSTRY APPLICATION

Extract as well as pharmaceutical composition of *Curcuma mangga* Val. et Zipp. extract can be made in industrial scale for the production of extract, dry powder extract, and/or pharmaceutical composition, especially for oral dosage forms, either solid, semi-solid, or liquid in its use as drugs of anti-BPH (prostate enlargement) and prostate cancer, via Prostate-Growth Reducer Pathway.

REFERENCE

Asada, Y., T. Sonoda, M. Ojiro, S. Kurata, T. Sato, T. Ezaki & Takayasu. 2001. 5{{alpha}}-reductase type 2 is constitutively expressed in the dermal papilla and connective tissue sheath of the hair follicle in vivo but not during culture in vitro. The Journal of Clinical Endocrinology & Metabolism 86: 2875-2880.

Beckman, T. J. & L. A. Mynderse. 2005. Evaluation and medical management of benign prostatic hyperplasia. Mayo Clinic Proceedings 80(10): 1356-1362.

Fei Ye, Shiquan Jiang, H. Volshonok, J. Wu & D. Y. Zhang. 2007. Molecular mechanism of anti-prostate cancer activity of Scutellaria baicalensis extract. Nutrition and Cancer 57(1): 100-110.

Fine, S. R. & P. Ginsberg. 2008. Alpha-andrenergic receptor antagonists in older patients with benign prostatic hyperplasia: Issues and potential complications. Journal of The American Osteopathic Association 108(7): 333-337.

Gjertson, C. J., K. Walmsley & S. A. Kaplan. 2004. Benign prostatic hyperplasia: Now we can begin to tailor treatment. Cleveland Clinic Journal of Medicine 71(11): 857-880.

Guess, H. A. 2001. Benign prostatic hyperplasia and prostate cancer. Epidemiologic Reviews 25(1): 152-158.

Gusmaini, M. Yusron & M. Januwati. 2004. Teknologi perbanyakan benih sumber temu mangga. Perkembangan Teknologi TRO Vol. XVI, No. 1.

Malek, S. N., G. S. Lee, S. L. Hong, H. Yaacob, N. A. Wahab, J. F. Faizal Weber, and S. A. Shah. 2011. Phytochemical and cytotoxic investigations of Curcuma mangga rhizomes. Molecules 16(6): 4539-48.

Nunez, R. 2001. DNA Measurement and cell cycle analysis by flow cytometry. Curr. Issues Mol. Biol. 3(3): 67-70.

Reynolds, R. J. & J. A. Schecker. 1995. Radiation, cell cycle, and cancer. Los Alamos Science 23: 51-89.

Rumiyati, Retno S. Sudibyo, Sismindari, Umar Anggara Jenie, Sofia Mubarika, L. Broto Kardono. 2007. Selective cytotoxicity of essential oil of Curcuma mangga Val. on cell lines and its effects on expressions of p53 and Bcl-2. Pudjono et al. (Eds.), Proceeding of The International Symposium on Recent Progress in Curcumin Research, Faculty of Pharmacy Gadjah Mada University Indonesia.

Sanda, M. G. & I. D. Kaplan. 2009. A 64-year-old man with low-risk prostate cancer. Journal of The American Medical Association 201(20): 2141-2151.

Schmidt, L. J., H. Murillo & D. J. Tindall. 2004. Gene expression in prostate cancer cells treated with the dual 5 alpha-reductase inhibitor dutasteride. Journal of Andrology 25(6): 944-952.

Smith, C. M., S. A. Ballard, N. Worman, R. Buettner & J. R. W. Masters. 1998. 5α-Reductase expression by prostate cancer cell lines and benign prostatic hyperplasia in Vitro. Journal of Clinical Endocrinology and Metabolism 81(4): 1361-1366.

Soderstrom, Torbjorn G., Catarina Bjelfman, Einar Brekkan, Brigitta Ask, Lars Egevad, Bo Johan Norlen and Anders Rane. 2001. Messenger ribonucleic acid levels of steroid 5α-reductase 2 in human prostate predict the enzyme activity. The Journal of Clinical Endocrinology & Metabolism 86 (2): 855.

Talcot, J. A., C. Rossi, W. U. Shipley, J. A. Clark, J. D. Slater, A. Niemierko, and A. L. Zietman. 2010. Patient-reported long-term outcomes after conventional and high-dose combined proton and photon radiation for early prostate cancer. The Journal of American Medical Association 303(11): 1046-53.

Tedjo, Aryo, Dondin Sajuthi, Latifah K. Darusman. 2005. Aktivitas Kemoprevensi Ekstrak Temu Mangga. Makara, Kesehatan, Vol. 9, No. 2, December 2005: 57-62.

Winter, R. A., A. Kramer, A. Borkowski & N. Kyprianou. 2001. Loss of caspase-1 and caspase-3 protein expression in human prostate cancer. Cancer Research 61: 1227-1232.

Yi Cai, Jianghua Wang & Rile Li. 2009. GGAP2/PIKE-A Directly activates both the Akt and Nuclear Factor-KB pathways and promotes prostate cancer progression. Cancer Res 69: 819-827.

The invention claimed is:

1. A method for treating benign prostatic hyperplasia (BPH), comprising administering to a patient suffering from BPH an effective amount of an extract of Curcuma mangga Val. et Zipp.,
wherein the extract contains less than 0.05% (w/w) curminoids and is obtained by the process comprising the steps of:
(a) Chopping dried Curcuma mangga Val. et Zipp. rhizome to a length of 3-7 mm;
(b) Extracting the chopped material from step (a) with maceration and/or percolation method using an extraction solvent comprising a C1-C4 alcohol,
wherein the solid-to-solvent ratio is (1:6)-(1:10) w/v, the duration of maceration and/or percolation is between 30-240 minutes, and the solids are filtered to obtain filtrate;
(c) Concentrating the filtrate from step (b) by evaporation until extract concentrate is obtained;
(d) Adding a filler to the extract concentrate from step (c);
(e) Drying the mixture of extract concentrate and filler from step (d) to obtain a dry extract; and
(f) Milling the dry extract from step (e).

2. The method of claim 1, wherein said extract reduces the gene expression of 5-alpha-reductase-1.

3. The method of claim 1, wherein said extract reduces the gene expression of androgen receptor.

4. The method of claim 1, wherein said extract inhibits the PI3 kinase and Akt pathways.

* * * * *